US011982436B2

(12) United States Patent
Oepts et al.

(10) Patent No.: US 11,982,436 B2
(45) Date of Patent: May 14, 2024

(54) MELANOPIC LED SYSTEM WITH COLLIMATED WHITE LIGHT AND UNCOLLIMATED CYAN LIGHT

(71) Applicant: SIGNIFY HOLDING B.V., Eindhoven (NL)

(72) Inventors: Wouter Oepts, Eindhoven (NL); Ryan Robert James Gates, Langley (CA); Yuanjing Peng, Shanghai (CN)

(73) Assignee: SIGNIFY HOLDING B.V., Eindhoven (NL)

(*) Notice: Subject to any disclaimer, the term of this patent is extended or adjusted under 35 U.S.C. 154(b) by 0 days.

(21) Appl. No.: 18/007,800

(22) PCT Filed: May 27, 2021

(86) PCT No.: PCT/EP2021/064206
§ 371 (c)(1),
(2) Date: Dec. 2, 2022

(87) PCT Pub. No.: WO2021/244942
PCT Pub. Date: Dec. 9, 2021

(65) Prior Publication Data
US 2023/0296223 A1 Sep. 21, 2023

(30) Foreign Application Priority Data

Jun. 2, 2020 (WO) .............. PCT/CN2020/0904023
Jun. 18, 2020 (EP) .................................. 20180843

(51) Int. Cl.
F21V 5/00 (2018.01)
A61N 5/06 (2006.01)
(Continued)

(52) U.S. Cl.
CPC ............ *F21V 5/007* (2013.01); *A61N 5/0618* (2013.01); *F21Y 2105/12* (2016.08); *F21Y 2113/13* (2016.08); *F21Y 2115/10* (2016.08)

(58) Field of Classification Search
CPC .. F21V 5/007; F21Y 2103/10; F21Y 2105/10; F21Y 2105/12; F21Y 2113/10; F21Y 2113/13; F21Y 2115/10
See application file for complete search history.

(56) References Cited

U.S. PATENT DOCUMENTS 4,254,453 A * 3/1981 Mouyard ................ G09F 13/22
345/82
4,914,731 A * 4/1990 Chen ..................... G09F 27/008
455/24

(Continued)

FOREIGN PATENT DOCUMENTS

WO 2012167800 A1 12/2012
WO 2013011410 A1 1/2013

Primary Examiner — Ismael Negron

(57) ABSTRACT

A light generating system including a first light source configured to generate a first light with a first spectral power distribution, a second light source configured to generate a second light with a second spectral power distribution different from the first spectral power distribution, and optics configured to beam shape at least the first light. The first light has a wavelength range of 380-780 nm, and the second light has a wavelength range of 470-490 nm. The light generating system is configured to provide in a first operational mode white first light in a first direction, and second light in a second direction.

15 Claims, 6 Drawing Sheets

(51) Int. Cl.
*F21Y 105/12* (2016.01)
*F21Y 113/13* (2016.01)
*F21Y 115/10* (2016.01)

(56) References Cited

U.S. PATENT DOCUMENTS

| | | | | |
|---|---|---|---|---|
| 7,557,781 B2* | 7/2009 | Chuang | .............. | G02B 6/0021 |
| | | | | 345/82 |
| 7,736,019 B2* | 6/2010 | Shimada | .............. | F21V 13/02 |
| | | | | 362/249.14 |
| 7,888,868 B2* | 2/2011 | Kuan | .............. | F21K 9/69 |
| | | | | 313/512 |
| 8,047,676 B2* | 11/2011 | Cheng | .............. | F21V 13/04 |
| | | | | 362/240 |
| 8,610,135 B2* | 12/2013 | Aoki | .............. | F21K 9/00 |
| | | | | 257/431 |
| 8,622,573 B2* | 1/2014 | Kubis | .............. | H05B 45/56 |
| | | | | 362/249.02 |
| 8,899,767 B2* | 12/2014 | Harbers | .............. | F21V 7/0025 |
| | | | | 362/231 |
| 11,162,662 B2* | 11/2021 | Wu | .............. | F21V 9/30 |
| 11,307,455 B2* | 4/2022 | Kasai | .............. | G02B 6/0021 |
| 2014/0160728 A1* | 6/2014 | Kim | .............. | F21K 9/64 |
| | | | | 362/84 |
| 2015/0062892 A1 | 3/2015 | Krames et al. | | |
| 2015/0267875 A1 | 9/2015 | Bates | | |
| 2015/0335246 A1 | 11/2015 | Rains, Jr. et al. | | |
| 2016/0193478 A1 | 7/2016 | Maxik et al. | | |
| 2018/0073689 A1 | 3/2018 | Soer et al. | | |
| 2018/0172227 A1 | 6/2018 | Soler et al. | | |
| 2018/0177017 A1 | 6/2018 | Soler et al. | | |
| 2018/0269360 A1 | 9/2018 | Yeon et al. | | |
| 2019/0267356 A1 | 8/2019 | Soler et al. | | |
| 2021/0270443 A1* | 9/2021 | Yun | .............. | F21V 9/38 |
| 2021/0329757 A1 | 10/2021 | Peeters et al. | | |

* cited by examiner

MELANOPIC LED SYSTEM WITH COLLIMATED WHITE LIGHT AND UNCOLLIMATED CYAN LIGHT

CROSS-REFERENCE TO PRIOR APPLICATIONS

This application is the U.S. National Phase application under 35 U.S.C. § 371 of International Application No. PCT/EP2021/064206, filed on May 27, 2021, which claims the benefit of International Application No. PCT/CN2020/094023, filed on Jun. 2, 2020 and European Patent Application No. 20180843.3, filed on Jun. 18, 2020. These applications are hereby incorporated by reference herein.

FIELD OF THE INVENTION

The invention relates to a light generating system. The invention further relates to a lamp or a luminaire comprising the light generating system.

BACKGROUND OF THE INVENTION

Lighting modules for generating white light with a specific melanopic flux are known in the art. US2018/0177017, for instance, describes a LED lighting module for generating illumination that produces white light with adequate melanopic flux, reduced blue light hazard flux and color uniformity comprising: one or more LED light sources, the lighting module being configured to emit, during operation of the system, light having a first spectral intensity profile in a wavelength range from 400 nm to 700 nm, wherein the total radiant power in a first wavelength band from 460 nm to 500 nm is greater than 14% of the total radiant power in said first spectral intensity profile and wherein the total radiant power in a second wavelength band from 500 nm to 700 nm is more than half of the total radiant power in the first spectral intensity profile and wherein the light emitted from said LED lighting module is substantially white light.

SUMMARY OF THE INVENTION

It appears that there is a desire for lighting that is focused on the needs of humans. This may be indicated a "Human Centric Lighting" (HCL). Human centric light may be useful as such lighting may improve well-being of humans, or improve alertness, or adopt the spectral power distribution to the time of the day. For instance, it appears to be possible to enable different atmosphere lighting or Melanopic boost that can be targeted to the user at a specific moment. In this way, e.g. school lighting to stimulate effectiveness of students depending on the activity may be provided. However, also the circadian rhythm in offices or hospitals may also promoted with human centric lighting. Solutions to increase the Melanopic lux (or Melanopic Daylight Efficiency Ration— MDER) appear to require a peak in the cyan light, around about 480 nm. Creating such spectrum may require a different LED solution than standard white LEDs. However, it appears that due to the differences in color of white and cyan, the light mixing of the colors may be difficult. This may imply an additional diffusor. However, with a diffusor light may be lost. Further, for lighting applications such as office light, a low glare may be required for visual comfort. In short, glare may be described as the phenomenon caused by very bright light sources or by strong brightness contrasts in the visual field. The impact of glare may be linked to the surface area, measured in Candela per square meter. But the experience of glare also depends on parameters like luminance contrasts in the visual field, on the viewer's age, the iris color and individual sensitivity to light. Achieving low glare appears to require beam shaping of the emitted light from the LEDs. Normally LEDs emit a Lambertian uniform emission, which may need to be collimated to direct the light more downward. One may e.g. use 3D lenses to collimate the LED light and then a sheet with patterns to mix the light a bit such that the individual LED sources are less visible. The result is that the emitted radiation is mostly downward and a low glare is achieved. The combination of 3D lenses and such patterned sheet may e.g. result in an optical efficiency (LOR) of above about 80%. A downside is that the lens plate is designed dedicated for the type of LEDs and the number of LEDs. Hence changing LED type and doubling LED count for tunable white requires new investments in lenses, or may even be impossible due to the minimal lens dimension. Alternatively, one may use a diffuser and e.g. micro lens optics. This may give a relatively nice uniform and collimated output. An advantage is that the LED count and types can be easily changed without the need to change the optical architecture. However the overall efficiency may be below about 70% and micro lens optics may be relatively expensive.

It surprisingly appears that the melanopic light sensitive area in the human eye is positioned in a specific part of the eye. It is most sensitive for light moving in the vertical plane. As a consequence, for people working and sitting in an office, the vertical illuminance is the metric used to express the melanopic value. However, this light direction is reduced by the requirements to have low glare luminaires. A low glare luminaire directs the light downward and has a low vertical illuminance value. Therefore, it was surprisingly found that for an efficient melanopic light increase, this light should be (primarily) emitted in the vertical direction, whilst the white light should be collimated to illuminate the desks properly with low glare.

Hence, it is an aspect of the invention to provide an alternative light generating device, which preferably further at least partly obviates one or more of above-described drawbacks. The present invention may have as object to overcome or ameliorate at least one of the disadvantages of the prior art, or to provide a useful alternative.

Amongst others, in embodiments the present invention proposes using LED boards with both white and cyan LEDs, and lens plates with lenses only on the white LEDs and not on the cyan LEDs. As a result, the white light is collimated and optimized for glare and horizontal illumination, whilst the cyan light (typically only about 10% of the total) is not collimated and will have a higher vertical illuminance.

In a first aspect, the invention provides a light generating system ("lighting system") comprising a first light source, a second light source, and optics. Especially, the first light source is configured to generate first light source light having in a first operational mode a first spectral power distribution. In embodiments, the first light source light has at least intensity at a plurality of wavelengths in a first wavelength range of 380-780 nm. Especially, the second light source is configured to generate second light source light having in the first operational mode a second spectral power distribution differing from the first spectral power distribution. In embodiments, the second light source light has at least intensity at one or more wavelengths in a second wavelength range of 470-490 nm. Alternatively or additionally, in embodiments, the second light source light has at least intensity at one or more wavelengths in a second wavelength range of 380-430 nm. Especially, the optics are configured to beam shape at least the first light source light.

The light generating system is configured to provide in a first operational mode white first system light in a first direction and second system light in a second direction. In embodiments, a relative intensity of the second light source light to the second system light is higher than the relative intensity of the second light source light to the first system light.

In embodiments, the light generating system comprises a plurality of first light sources, a plurality of second light sources, and optics. The light sources may be configured in an array (or in respective arrays), such as an 1D array. The optics may comprise beam shaping elements, which may also be configured in an array, such as an 1D array. In embodiments (see also above) the first light sources are configured to generate first light source light having in a first operational mode a first spectral power distribution, wherein the first light source light has at least intensity at a plurality of wavelengths in a first wavelength range of 380-780 nm. Especially, in embodiments the first light sources may be configured in a first array having a first pitch (P1). Further, in embodiments the second light sources are configured to generate second light source light having in the first operational mode a second spectral power distribution differing from the first spectral power distribution, wherein the second light source light has at least intensity at one or more wavelengths in a second wavelength range of one or more of (i) 380-430 nm and (ii) 470-490 nm. Especially, in embodiments the second light sources may be configured in a second array having a second pitch (P2). In specific embodiments, the optics may comprise a plurality of beam shaping elements configured to beam shape at least the first light source light. In specific embodiments, the beam shaping elements may be configured in a third array having a third pitch (P3), such as an 1D array. In embodiments, the beam shaping elements have a first diameter (D) (which may in embodiments also refer to an equivalent circular diameter). In specific embodiments, P1=P3. Further, in specific embodiments, P2≥P1. Yet further, in specific embodiments D/P1≤1, even more especially 0.5≤D/P1≤1, such as especially 0.6≤D/P1≤1.

With such light generating system(s), glare conditions can be met, white light may be provided in a vertical direction, e.g. for use on a desk, and in a (more) vertical direction light may be provided that is (relatively more) enriched with cyan light. Hence, the MDER values in different directions may differ. In this way, a more efficient MDER light generating system may be provided. Further, it still may be possible to have the presence of cyan light sources essentially invisible for a user.

Alternatively, when second light source light having a wavelength selected from the 380-430 nm is applied, such light may be used for disinfection purposes.

In specific embodiments, light generating system comprising a first light source, a second light source, and optics, wherein: (a) the first light source is configured to generate first light source light having in a first operational mode a first spectral power distribution, wherein the first light source light has at least intensity at a plurality of wavelengths in a first wavelength range of 380-780 nm; (b) the second light source is configured to generate second light source light having in the first operational mode a second spectral power distribution differing from the first spectral power distribution, wherein the second light source light has at least intensity at one or more wavelengths in a second wavelength range of 470-490 nm; (c) the optics are configured to beam shape at least the first light source light; (d) the light generating system is configured to provide in a first operational mode white first system light in a first direction and second system light in a second direction; (e) the first system light in the first direction comprises the first light source light and the second light source light; (f) the second system light in the second direction at least comprises the second light source light; and (g) a relative intensity of the second light source light to the second system light is higher than the relative intensity of the second light source light to the first system light.

Yet, in further embodiments the invention provides light generating system comprising a plurality of first light sources, a plurality of second light sources, and optics, wherein: (a) the first light sources are configured to generate first light source light having in a first operational mode a first spectral power distribution, wherein the first light source light has at least intensity at a plurality of wavelengths in a first wavelength range of 380-780 nm; wherein the first light sources are configured in a first array having a first pitch (P1); (b) the second light sources are configured to generate second light source light having in the first operational mode a second spectral power distribution differing from the first spectral power distribution, wherein the second light source light has at least intensity at one or more wavelengths in a second wavelength range of one or more of (i) 380-430 nm and (ii) 470-490 nm; wherein the second light sources are configured in a second array having a second pitch (P2); (c) the optics comprise a plurality of beam shaping elements configured to beam shape at least the first light source light; wherein the beam shaping elements are configured in a third array having a third pitch (P3), and wherein the beam shaping elements have a first diameter (D); and (d) P1=P3 and P2≥P1 and 0.6≤D/P1≤1.

Especially, the first system light in the first direction comprises the first light source light and the second light source light, wherein the first system light has a first ratio R1 of luminous flux in the second wavelength range relative to the luminous flux in the first wavelength range. Further, the second system light in the second direction at least comprises the second light source light, wherein the second system light has a second ratio R2 of luminous flux in the second wavelength range relative to the luminous flux in the first wavelength range. The ratio R2/R1>1, such as R2/R1≥2 in embodiments. Hence, especially the invention provides in embodiments a light generating system comprising a first light source, a second light source, and optics, wherein: (a) the first light source is configured to generate first light source light having in a first operational mode a first spectral power distribution, wherein the first light source light has at least intensity at a plurality of wavelengths in a first wavelength range of 380-780 nm; (b) the second light source is configured to generate second light source light having in the first operational mode a second spectral power distribution differing from the first spectral power distribution, wherein the second light source light has at least intensity at one or more wavelengths in a second wavelength range of 470-490 nm; (c) the optics are configured to beam shape at least the first light source light; (d) the light generating system is configured to provide in a first operational mode white first system light in a first direction and second system light in a light and the second light source light, wherein the first system light has a first ratio R1 of luminous flux in the second wavelength range relative to the luminous flux in the first wavelength range; and (f) the second system light in the second direction at least comprises the second light source light, wherein the second system light has a second ratio R2 of luminous flux in the second wavelength range relative to the luminous flux in the first wavelength range, wherein R2/R1>1.

Alternatively or additionally, In specific embodiments, light generating system comprising a first light source, a second light source, and optics, wherein: (a) the first light source is configured to generate first light source light having in a first operational mode a first spectral power distribution, wherein the first light source light has at least intensity at a plurality of wavelengths in a first wavelength range of 380-780 nm; (b) the second light source is configured to generate second light source light having in the first operational mode a second spectral power distribution differing from the first spectral power distribution, wherein the second light source light has at least intensity at one or more wavelengths in a second wavelength range of 380-430 nm; (c) the optics are configured to beam shape at least the first light source light; (d) the light generating system is configured to provide in a first operational mode white first system light in a first direction and second system light in a second direction; (e) the first system light in the first direction comprises the first light source light and the second light source light; (0 the second system light in the second direction at least comprises the second light source light; and (g) a relative intensity of the second light source light to the second system light is higher than the relative intensity of the second light source light to the first system light. Second light having a wavelength selected from the range of 380-430 nm, such as selected from the range of about 395-425 nm, may e.g. be used for disinfection purposes.

Hence, the relative intensities of the first light source light and second light source light may differ in dependence of an angle relative to a normal to the light generating system, such as relative to a normal to a luminaire. Especially, along the normal the ratio of the second light source light to the first light source light (comparing the intensities in power, such as Watts) is smaller than at non-zero angles to such normal, where such ratio may be larger.

In specific embodiments, the second light source light is enriched (relatively more power) in the second wavelength range relative to the first light source light. Or, the first light source light is depleted (relatively less power) in the second wavelength range relative to the second light source light. In specific embodiments (see also below), the second light source light may essentially consist of light having wavelengths in the 380-430 nm or in the 470-490 nm wavelength range. Here below, especially the invention is explained in relation to second light source light that is essentially cyan light (470-490 nm light), or that is (white light) enriched with cyan light.

As indicated above, the light generating system comprises a first light source, a second light source, and optics. These items are further discussed below in general and in more detail, respectively.

The term "light source" may refer to a semiconductor light-emitting device, such as a light emitting diode (LEDs), a resonant cavity light emitting diode (RCLED), a vertical cavity laser diode (VCSELs), an edge emitting laser, etc. The term "light source" may also refer to an organic light-emitting diode, such as a passive-matrix (PMOLED) or an active-matrix (AMOLED). In a specific embodiment, the light source comprises a solid state light source (such as a LED or laser diode). In an embodiment, the light source comprises a LED (light emitting diode). The term LED may also refer to a plurality of LEDs. Further, the term "light source" may in embodiments also refer to a so-called chips-on-board (COB) light source. The term "COB" especially refers to LED chips in the form of a semiconductor chip that is neither encased nor connected but directly mounted onto a substrate, such as a PCB. Hence, a plurality of semiconductor light sources may be configured on the same substrate. In embodiments, a COB is a multi LED chip configured together as a single lighting module. The term "light source" may also relate to a plurality of (essentially identical (or different)) light sources, such as 2-2000 solid state light sources. In embodiments, the light source may comprise one or more micro-optical elements (array of micro lenses) downstream of a single solid state light source, such as a LED, or downstream of a plurality of solid state light sources (i.e. e.g. shared by multiple LEDs). In embodiments, the light source may comprise a LED with on-chip optics. In embodiments, the light source comprises a pixelated single LEDs (with or without optics) (offering in embodiments on-chip beam steering).

The phrases "different light sources" or "a plurality of different light sources", and similar phrases, may in embodiments refer to a plurality of solid state light sources selected from at least two different bins. Likewise, the phrases "identical light sources" or "a plurality of same light sources", and similar phrases, may in embodiments refer to a plurality of solid state light sources selected from the same bin.

The terms "upstream" and "downstream" relate to an arrangement of items or features relative to the propagation of the light from a light generating means (here the especially the light source), wherein relative to a first position within a beam of light from the light generating means, a second position in the beam of light closer to the light generating means is "upstream", and a third position within the beam of light further away from the light generating means is "downstream".

Especially, the first light source is configured to generate first light source light having in a first operational mode a first spectral power distribution, wherein the first light source light has at least intensity at a plurality of wavelengths in a first wavelength range of 380-780 nm. Especially, the first light source light is white light.

The term "white light" herein, is known to the person skilled in the art. It especially relates to light having a correlated color temperature (CCT) between about 1800 K and 20000 K, such as between 2000 and 20000 K, especially 2700-20000 K, for general lighting especially in the range of about 2700 K and 6500 K. In embodiments, for backlighting purposes the correlated color temperature (CCT) may especially be in the range of about 7000 K and 20000 K. Yet further, in embodiments the correlated color temperature (CCT) is especially within about 15 SDCM (standard deviation of color matching) from the BBL (black body locus), especially within about 10 SDCM from the BBL, even more especially within about 5 SDCM from the BBL. The terms "visible", "visible light" or "visible emission" and similar terms refer to light having one or more wavelengths in the range of about 380-780 nm.

Especially, the first light source may have a CCT selected from the range of 3500-6500 K, a CRI selected from the range of at least about 80. In embodiments, R9 may be selected from the range of >−5, such as about at least 0. Hence, in embodiments the first light source light is white light.

Especially, the first light source comprises a solid state light source, more especially a LED. As further elucidated below, the light generating system may comprise a plurality of first light sources.

When a plurality of first light sources is applied, they may all have essentially the same CCT. However, in other embodiments two or more sets of different first light sources may be applied, differing in CCT, such as differing with at least 500 K, like differing at least about 1000 K. For instance, in embodiments a first set of first light sources may have a CCT selected from the range of 2800-3200 K, such as about 3000 K, and a second set of first light sources may have a CCT selected from the range of 3800-4200 K, such as about 4000 K or 4200 K. Hence, in embodiments two or more sets of different first light sources may be applied, which may be from different bins. However, the first light sources of the two or more sets may especially be configured to generate white light (as further described herein).

Further, especially, the second light source is configured to generate second light source light having in the first operational mode a second spectral power distribution differing from the first spectral power distribution, wherein the second light source light has at least intensity at one or more wavelengths in a second wavelength range of 470-490 nm. Especially, the second light source is configured to generate second light source light having a relatively large cyan content. The second light source light may be white light, but will in general be colored light, such as with a strong, or essentially only cyan hue. Hence, in embodiments at least 80% of the total power of the second light source light (in the visible wavelength range) is within the second wavelength range. Hence, a percentage of the power in the 470-490 nm relative to the total power in the 380-780 nm of the second light source light may especially be at least 80%, such as even more especially at least 90%. In specific embodiments, the second light source light has a dominant wavelength selected from the range of 478-484 nm. Hence, in embodiments at least 80% of the total power in the visible (of the second light source light) will be found in the 470-490 nm wavelength range.

In alterative embodiments, the second light may have a peak wavelength selected from the range of 380-430 nm, even more especially 385-430 nm, such as selected from the range of 395-425 nm. Even more especially, the peak wavelength of the second light may in embodiments selected from the range of 395-420 nm, such as 400-415 nm. Hence, in embodiments at least 80% of the total power of the second light source light (in the visible wavelength range) is within the second wavelength range. Hence, a percentage of the power in the 380-430 nm relative to the total power in the 380-780 nm of the second light source light may especially be at least 80%, such as even more especially at least 90%. In specific embodiments, the second light source light has a dominant wavelength selected from the range of 395-420 nm. Hence, in embodiments at least 80% of the total power in the visible (of the second light source light) will be found in the 380-430 nm wavelength range, such as 395-420 nm.

The term "dominant wavelength" may refer to the wavelength of the monochromatic stimulus that, when additively mixed in suitable proportions with the specified achromatic stimulus, matches the color stimulus considered.

Especially, the second light source comprises a solid state light source, more especially a LED. As further elucidated below, the light generating system may comprise a plurality of second light sources.

The light generating system may further comprise optics. Especially, the optics are configured to beam shape at least the first light source light. In embodiments, the optics are configured to reduce glare of at least the first light source light. Hence, in embodiments the optics may be configured to provide a beam of first light source light having full width half maximum at maximum of about 65° from a normal to the first light source (or an exit window of the light generating device). Especially, in embodiments the unified glare rating (UGR) is 19 or smaller.

The light generating system is configured to generate system light. As indicated above, and also further elucidated below, there may be an angular dependence of the spectral power distribution, such as relative to a normal to an exit window of the light generating device. The change may be gradual with changing angle. Herein, two types of system light are described, for the sake of understanding, which are indicated with first system light and second system light. In general, the former is the system light along an optical axis of the system light and/or a normal to an exit window of the light generating device and the latter may refer to the system light under specific angles relative to the optical axis of the system light and/or a normal to an exit window of the light generating device.

The phrase "relative to a normal" and similar phrases may e.g. refer to embodiments such as a normal relative to al luminaire. For instance, the light generating system may have an exit window, from which the system light may escape. The normal may be perpendicular to such exit window. This may be an exit window of a luminaire.

In embodiments, the light generating system is configured to provide in a first operational mode white first system light in a first direction and second system light in a second direction. Especially, the spectral power distributions of the first system light and the second system light are different.

In specific embodiments, the light generating system is configured to provide the first light source light and the second light source light, and thus also the first system light and the second system light within a cone having angles to a cone axis (or normal to the exit window of the light generating device) equal to or smaller than 90°. For instance, the light generating system may be used as downlight and may in embodiments not have an uplighting functionality.

The fact that the light generating system is configured to provide in a first operational mode white first system light in a first direction and second system light in a second direction may not exclude that there may also different direction in which the first system light and the second system light are essentially the same. However, there are at least two directions, and in general a plurality of directions wherein the light generating system is configured to provide in a first operational mode white first system light in a first direction and second system light in a second direction, wherein the spectral power distributions differ (such as also indicated with the ratios, see below). Assuming the first system light to have an optical axis, especially under angles relative to this optical axis, the spectral power distribution in one or more other directions may differ from the spectral power distribution of the system light along the optical axis. Especially, the spectral power distribution may differ at larger angles from the normal (see also below).

In embodiments, the first system light in the first direction comprises the first light source light and the second light source light. In such embodiments, the first system light in the second wavelength range may primarily be provided by the second light source light. However, it is not excluded that the second light source light also has intensity in the wavelength range of 380-780 nm other than the second wavelength range.

The first system light has a first ratio R1 of luminous flux in the second wavelength range relative to the luminous flux in the first wavelength range. In embodiments, the first ratio R1 may be selected from the range of 0.01-0.15. Hence, about 10% of the lumens of the first system light may be cyan type of light.

In (further) embodiments, the second system light in the second direction at least comprises the second light source light, which second light source light may essentially be cyan light. However, it is not excluded that the second system light also comprise first light source light. In such embodiments, the second system light in the second wavelength range may essentially be provided by the second light source light. However, as indicated above, it is not excluded that the second light source light also has intensity in the wavelength range of 380-780 nm other than the second wavelength range. Further, it is also not excluded that the second system light has intensity in the 380-780 nm wavelength range contributed by the first light source light.

The second system light has a second ratio R2 of luminous flux in the second wavelength range relative to the luminous flux in the first wavelength range. In embodiments, the second ratio R2 may be selected from the range of 0.2-15, such as selected from the range of 0.2-5, like in specific embodiments selected from the range of 0.2-3. Hence, at least about 20% of the lumens of the second system light may be cyan type of light.

The ratio R2/R1>1. In other words, in embodiments the cyan contribution in % of the total power of the system light in the second direction is larger than of the system light in the first direction. Especially, in embodiments R2/R1≥2.

Under a first angle ($\alpha1$) relative to (a normal N to) the light generating system the first ratio R1 may (thus) be selected from the range of 0.01-0.15. Under a second angle ($\alpha2$) relative to (the normal N to) the light generating system the second ratio R2 is selected from the range of 0.2-15, preferably from the range 0.2-5. Even more especially, $\alpha2|=80°\pm5°$. The value of the difference in angles may in general not mean a binary transition from the first system light at the first angle to the second system light at the second angle, but will in general be a gradual change wherein the R2/R1 is lower at $\alpha1$, such as at about 0° relative to a normal, and larger at $\alpha2$, such as at about 80°. Especially, in embodiments, wherein the second light source may especially be configured to generate cyan second light source light, R2/R1 may be selected from the range of 0.2-5, especially at $|\alpha1-\alpha2|=80°\pm5°$. Even more especially, in embodiments R2/R1 may be selected from the range of 0.2-3, especially at $|\alpha1-\alpha2|=80°\pm5°$, such as in embodiments 0.3-3.

In specific embodiments, especially wherein the second light source light may essentially be in the 470-490 nm range, the cyan/white ratio (ratio of the power in the cyan wavelength range of 470-490 nm) relative to the total intensity of the (second) system light, at angles of about 80° (relative to a normal to the system), may be selected from the range of about 1:5-5:1, such as 1:5-3:1.

As indicated above, the first light source and/or the second light source may especially be solid state light sources. Such light sources may have a light emitting surface, such as a dye, a phosphor, a lens, etc. Hence, the light sources may have light emitting faces. Further, the light sources may have optical axes, which may especially be perpendicular to (part) of such light emitting face, respectively. Especially, even though the first system light and the second system light may have different spatial (power) distributions, such optical axis emanating from the respective light sources may essentially be parallel. Hence, in embodiments the first light source has a first light emitting face and a first optical axis (O1) configured perpendicular to the light emitting face, wherein the second light source has a second light emitting face and a second optical axis (O2) configured perpendicular to the second light emitting face, wherein the first optical axis (O1) and the second optical axis (O2) are configured colinear. As indicated above, especially the first light source is a solid state light source and the second light source is a solid state light source. Especially, the solid state dies may provide light emitting faces.

More especially, the light generating system may comprise an array of first light sources and second light sources. Especially, in such array the plurality of first light sources may essentially be identical. However, they may also differ, as far as they comply with the herein described conditions for the first light source(s). Likewise, in such array the plurality of second light sources may essentially be identical. However, they may also differ, as far as they comply with the herein described conditions for the second light source(s). Hence, in specific embodiments the light generating system may comprise (i) a plurality of first light sources and a plurality of second light sources; (ii) the first light sources and the second light sources are configured in an array, wherein one or more first light sources alternate with one or more second light sources, wherein the plurality of first light sources are configured in a first array and the plurality of second light sources are configured in a second array; and (iii) the optics comprise a plurality of beam shaping elements configured in a third array, wherein the beam shaping elements are configured downstream of the first light sources.

In embodiments, the beam shaping elements are selected from the group consisting of lenses, reflectors and collimators. When the beam shaping elements comprise collimators, especially these collimators comprise light transparent solid bodies. When the beam shaping elements comprise reflectors, these may be hollow reflectors.

Especially, the beam shaping elements may essentially be configured for collimating the first light source light though in embodiments they may also collimate at least part of the second light source light. Hence, in embodiments there may only be beam shaping elements that primarily beam shape the first light source light and no beam shaping elements that primarily beam shape the second light source light (see further also below).

In embodiments, the beam shaping elements may be configured to provide first system light having a full width half maximum at a maximum about 2*50° (beam angle of at maximum about 50°), such as at maximum about 2*40° full width half maximum (beam angle of at maximum about 40°). The solid state light sources as such, may have a full width half maximum at a maximum about 2*60° (beam angle of at maximum about 60°), which may be a Lambertian type distribution. Hence, the beam shaping elements may be used to collimate the first light source light.

Especially, first system light is the light of the system parallel to a normal to the system. Especially, this may be light essentially perpendicular to the solid state light sources (dies) and essentially parallel to optical axes of the beam shaping elements.

Hence, the first light source light may be collimated. In embodiments, the beam shaping elements may be configured to provide the first light source light having a full width half maximum at a maximum about 2*50° (beam angle of at maximum about 50°), such as at maximum about 2*40° full width half maximum (beam angle of at maximum about 40°). The second light source light may be subject to a smaller degree of collimation, or may even not be collimated at all. In embodiments, the second light source light may have may even be decollimated. In embodiments, the second light source light downstream of the beam shaping elements may have a full width half maximum of more than 2*60° (beam angle more than 60°).

In embodiments, the first light sources in the first array have a first pitch (P1), the second light sources in the second array have a second pitch (P2), and the beam shaping elements in the third array have a third pitch (P3). Especially, in embodiments P1≈P3, more especially P1=P3. Especially, in embodiments P1=P3 and P2≥P1. For instance, in embodiments 2≤P2/P1≤6, such as P2=2×P1, or P2=3×P1 or P2=4×P1.

Herein, the array(s) may be 1D arrays or 2D arrays.

The beam shaping elements will in general have an essentially circular cross-section, though other cross-sections may also be possible. Hence, the beam shaping elements have a first diameter (D). For beam shaping elements not having an essentially circular cross-section, the equivalent circular diameter (D) may be applied. The equivalent circular diameter (or ECD) of an (irregularly shaped) two-dimensional shape is the diameter of a circle of equivalent area. For instance, the equivalent circular diameter of a square with side a is $2*a*SQRT(1/\pi)$. For a circle, the diameter is the same as the equivalent circular diameter. Would a circle in an xy-plane with a diameter D be distorted to any other shape (in the xy-plane), without changing the area size, than the equivalent circular diameter of that shape would be D. Especially, the term "diameter" (such as in embodiment the equivalent circular diameter) refers to the largest cross-section. Further, this term may also refer to a cross-section essentially perpendicular to the optical axis to the light source (and/or to an optical axis of the beam shaping element.

In embodiments, D/P1≤1, such as 0.5≤D/P1≤1. Especially, in embodiments wherein 0.6≤D/P1≤1. Even more especially, 0.9≤D/P1≤1. In such embodiments, the beam shaping elements may be configured downstream of the first light sources, with e.g. the optical axes of the beam shaping elements coinciding with the optical axes of the first light sources. In such embodiments, the beam shaping element and the first light sources may provide a first grid, and the second light sources may be configured between the first light sources at a subset of all intermediate positions (or at all intermediate positions). When D/P1 is larger than 0.5, this may imply that there may be no separate lens for the second light source(s). Hence, downstream of the second light source there may be no lens or downstream of the second light source there may be part of one or more adjacent lenses that are configured to collimate the first light source light of adjacent first light sources.

Further, in embodiments P2≤4 cm, such as especially P2≤3.5 cm. This may also add to the invisibility of the individual second light sources (when switched on). However, in specific embodiments P2>0.1 mm, such as at least about 0.2 mm. However, other dimensions may also be possible. Especially, in embodiments P2>P1.

In general, the equivalent circular diameters based on the cross-sections of the (solid state) light sources will in general be smaller than D. In general, they may be at maximum about 0.5*D. Or, in other words, the equivalent circular diameter of the beam shaping elements may be about at least twice, such as about at least three time, as large as the equivalent circular diameter of the first (solid state) light sources. Even more especially, in embodiments they may be about at least 5 times as large as the equivalent circular diameter of the (solid state) light sources, such as at least 10 times.

Even though the beam shaping elements may be configured essentially downstream of the first light sources, in embodiments it is not excluded that part of the (respective) beam shaping element is also configured downstream of the second light sources. Hence, in embodiments the beam shaping elements may also be at least partly configured downstream of the second light sources.

More especially, in embodiments the second light sources in the second array and the beam shaping elements (in the third array 153) are configured such that for a plurality of the second light sources in the second array applies that part of its second light source light propagates through a first beam shaping element configured downstream of a first adjacent first light source and part of its second light source light propagates through a second beam shaping element configured downstream of a second adjacent first light source. Herein, the phrase "for a plurality of the second light sources" is applied, as at the edges this may not always be the case. However, this may apply for a majority of the second light sources. Hence, in an embodiment a grid of first light sources and associated beam shaping elements may be provided, wherein a plurality of second light sources is configured between first light sources, thereby forming a second grid.

Therefore, in embodiments for the second light sources within the plurality of second light sources may apply that they are configured between the respective first adjacent first light source and the respective second adjacent first light source. More especially, in embodiments for one or more second light sources may apply that they are configured between the respective first adjacent first light source, the respective second adjacent first light source, an (respective) third adjacent first light source and optionally a (respective) fourth adjacent first light source.

Yet further especially, thus for one or more of the second light sources in the second array may apply that part of its second light source light propagates through a first beam shaping element configured downstream of a first adjacent first light source, part of its second light source light propagates through a second beam shaping element configured downstream of a second adjacent first light source, part of its second light source light propagates through a third beam shaping element configured downstream of a third adjacent first light source, and optionally part of its second light source light propagates through a fourth beam shaping element configured downstream of a fourth adjacent first light source.

The beam shaping elements may be provided as plate ("lens plate") comprising a plurality of lenses. Such plate may include a plurality of lenses, wherein in embodiments each lens may have an equivalent circular diameter of at least about 0.5 mm, though other dimensions may also be possible. The lens plate may e.g. include at least 10, such as at least 12, like in embodiments at least 20, such as at least 24, lenses. The lens plate, such as a lens strip, may be rigid or flexible. In specific embodiments, each lens may have an equivalent circular diameter of at least about 0.75 mm, such as selected from the range of about 0.75-5 mm, like 0.75-2 mm. Such lens plate may include a linear arrangement of lenses. Hence, in embodiments the beam shaping elements may be provided as lens strip. This may especially be the case when the first light sources and second light sources are configured in a 1D array. Such lens plate may in other embodiments also include a 2D array of lenses.

For other embodiments of the beam shaping elements may also apply that each lens may have an equivalent circular diameter of at least about 0.5 mm. Further, an array of beam shaping elements may e.g. include at least 10, such as at least 12, like in embodiments at least 20, such as at least 24, beam shaping elements, such as lenses, reflectors or collimators.

Hence, in embodiments no micro lens optics (MLO) may be applied, but lens plates with lenses having an equivalent circular diameter of at least about 0.5 mm. As indicated above, the lenses are especially configured downstream of the first light sources.

Optionally, a diffusor may be configured downstream of the beam shaping elements. Hence, in specific embodiments the beam shaping elements may comprise lenses, wherein the light generating system further comprises a diffusor configured downstream of the beam shaping elements. Such diffusor may comprise a light transmissive layer, such as a plate or foil, including structures that diffuse the light. Such structures may have dimensions smaller than the solid state light sources. Such diffusor may be use to inhibit visibility of the optical elements from external of the light generating system, such as at a distance of 3 m, while allowing transmission, such as transmission of essentially all light reaching such diffusor.

As indicated above, the second light source light of a specific second light source may propagate through parts of two or more beam shaping elements. Hence, in specific embodiments the lenses comprise lens edges, wherein the second light sources and the lenses are configured such that part of the second light source light propagates through the lens edges. In yet further specific embodiments, the lens edges may have a higher roughness than the lenses have in average. For instance, the lens edge may have an Ra roughness of at least about 0.4 µm, such as at least about 0.5 µm. In average, the Ra roughness of the lens may be smaller than about 0.4 µm, such as smaller than about 0.3 µm. At least part of the lens, especially a central part, may have an Ra roughness of 0.2 µm or smaller, such as about 0.1 µm. In embodiments, roughness may be created using sandblasting, chemical etching, or discharging.

In embodiments, the first light source(s) and the second light source(s) may be controlled. Even more especially, they may be controlled individually. In this way, the spectral power distribution of the system light may be controlled. For instance, in this way the first light sources configured to generate white light and the second light sources configured to generate (essentially) radiation in the wavelength range of 380-430 and/or in the wavelength range of 470-490 may individually be controlled.

As indicated above, in embodiments the light generating system may comprise a first light source, a second light source, and optics, wherein: (a) the first light source is configured to generate first light source light having in a first operational mode a first spectral power distribution, wherein the first light source light has at least intensity at a plurality of wavelengths in a first wavelength range of 380-780 nm; (b) the second light source is configured to generate second light source light having in the first operational mode a second spectral power distribution differing from the first spectral power distribution, wherein the second light source light has at least intensity at one or more wavelengths in a second wavelength range of 380-430 nm; (c) the optics are configured to beam shape at least the first light source light; (d) the light generating system is configured to provide in a first operational mode white first system light in a first direction and second system light in a light and the second light source light; (f) the second system light in the second direction at least comprises the second light source light; and (g) a relative intensity of the second light source light to the second system light is higher than the relative intensity of the second light source light to the first system light.

In embodiments, the first system light may have a first ratio $R'1$ of spectral power in the second wavelength range relative to the spectral power in the first wavelength range. Further, in embodiments the second system light has a second ratio $R'2$ of the spectral power in the second wavelength range relative to the spectral power in the first wavelength range, wherein $R'2/R'1>1$, especially wherein $R'2/R'1 \geq 2$.

Especially, in embodiments under a first angle ($\alpha 1$) relative to (a normal N to) the light generating system the first ratio $R'1$ may (thus) be selected from the range of 0.01-0.15. Alternatively or additionally, under a second angle ($\alpha 2$) relative to (the normal N to) the light generating system the second ratio $R'2$ is selected from the range of 0.2-15. Even more especially, $|\alpha 1-\alpha 2|=80°\pm 5°$. The value of the difference in angles may in general not mean a binary transition from the first system light at the first angle to the second system light at the second angle, but will in general be a gradual change wherein the $R'2/R'1$ is lower at $\alpha 1$, such as at about 0° relative to a normal, and larger at $\alpha 2$, such as at about 80°. Especially, in embodiments $R'2/R'1$ may be selected from the range of 0.2-5, especially at $|\alpha 1-\alpha 2|=80°\pm 5°$. Even more especially, in embodiments $R'2/R'1$ may be selected from the range of 0.2-3, especially at $|\alpha 1-\alpha 2|=80°\pm 5°$, such as in embodiments 0.3-3.

In embodiments, under a first angle ($\alpha 1$) relative to (a normal N to) the light generating system the first ratio $R'1$ is selected from the range of 0.05-0.4, wherein under a second angle ($\alpha 2$) relative to (the normal N to) the light generating system the second ratio $R'2$ is selected from the range of 0.3-10. For instance, $R'1$ may be selected from the range of 0.1-0.3 and $R'2$ may be selected from the range of 0.35-5.

The term "controlling" and similar terms especially refer at least to determining the behavior or supervising the running of an element. Hence, herein "controlling" and similar terms may e.g. refer to imposing behavior to the element (determining the behavior or supervising the running of an element), etc., such as e.g. measuring, displaying, actuating, opening, shifting, changing temperature, etc. Beyond that, the term "controlling" and similar terms may additionally include monitoring. Hence, the term "controlling" and similar terms may include imposing behavior on an element and also imposing behavior on an element and monitoring the element. The controlling of the element can be done with a control system, which may also be indicated as "controller". The control system and the element may thus at least temporarily, or permanently, functionally be coupled. The element may comprise the control system. In embodiments, the control system and element may not be physically coupled. Control can be done via wired and/or wireless control. The term "control system" may also refer to a plurality of different control systems, which especially are functionally coupled, and of which e.g. one control system may be a master control system and one or more others may be slave control systems. A control system may comprise or may be functionally coupled to a user interface.

The control system may also be configured to receive and execute instructions form a remote control. In embodiments, the control system may be controlled via an App on a device, such as a portable device, like a Smartphone or I-phone, a tablet, etc. The device is thus not necessarily coupled to the lighting system, but may be (temporarily) functionally coupled to the lighting system.

Hence, in embodiments the control system may (also) be configured to be controlled by an App on a remote device.

In such embodiments the control system of the lighting system may be a slave control system or control in a slave mode. For instance, the lighting system may be identifiable with a code, especially a unique code for the respective lighting system. The control system of the lighting system may be configured to be controlled by an external control system which has access to the lighting system on the basis of knowledge (input by a user interface of with an optical sensor (e.g. QR code reader) of the (unique) code. The lighting system may also comprise means for communicating with other systems or devices, such as on the basis of Bluetooth, WIFI, LiFi, ZigBee, BLE or WiMAX, or another wireless technology.

The system, or apparatus, or device may execute an action in a "mode" or "operation mode" or "mode of operation". Likewise, in a method an action or stage, or step may be executed in a "mode" or "operation mode" or "mode of operation" or "operational mode". The term "mode" may also be indicated as "controlling mode". This does not exclude that the system, or apparatus, or device may also be adapted for providing another controlling mode, or a plurality of other controlling modes. Likewise, this may not exclude that before executing the mode and/or after executing the mode one or more other modes may be executed.

However, in embodiments a control system may be available, that is adapted to provide at least the controlling mode. Would other modes be available, the choice of such modes may especially be executed via a user interface, though other options, like executing a mode in dependence of a sensor signal or a (time) scheme, may also be possible. The operation mode may in embodiments also refer to a system, or apparatus, or device, that can only operate in a single operation mode (i.e. "on", without further tunability).

Hence, in embodiments, the control system may control in dependence of one or more of an input signal of a user interface, a sensor signal (of a sensor), and a timer. The term "timer" may refer to a clock and/or a predetermined time scheme.

In specific embodiments, the first light sources may be available in one or more LED strings and the second light sources may be available in one or more other LED strings. Hence, in embodiments the light generating system may comprise (a) a first LED string comprising the plurality of first light sources; (b) a second LED string comprising the plurality of second light sources; and (c) a control system configured to control the first LED string and the second LED string (individually).

In yet a further aspect, the invention provides a lamp or a luminaire comprising the light generating system as defined herein. The luminaire may further comprise a housing, optical elements, louvres, etc. etc. . . . . . The lamp or luminaire may further comprise a housing enclosing the first light generating device, the second light generating device, and the optional third light generating device. The lamp or luminaire may comprise a light window in the housing or a housing opening, through which the system light may escape from the housing.

The light generating system may be part of or may be applied in e.g. office lighting systems, household application systems, shop lighting systems, home lighting systems, accent lighting systems, spot lighting systems, theater lighting systems, fiber-optics application systems, projection systems, self-lit display systems, pixelated display systems, segmented display systems, warning sign systems, medical lighting application systems, indicator sign systems, decorative lighting systems, portable systems, automotive applications, (outdoor) road lighting systems, urban lighting systems, green house lighting systems, horticulture lighting, digital projection, or LCD backlighting.

BRIEF DESCRIPTION OF THE DRAWINGS

Embodiments of the invention will now be described, by way of example only, with reference to the accompanying schematic drawings in which corresponding reference symbols indicate corresponding parts, and in which.

DETAILED DESCRIPTION OF THE EMBODIMENTS

Figure 1:
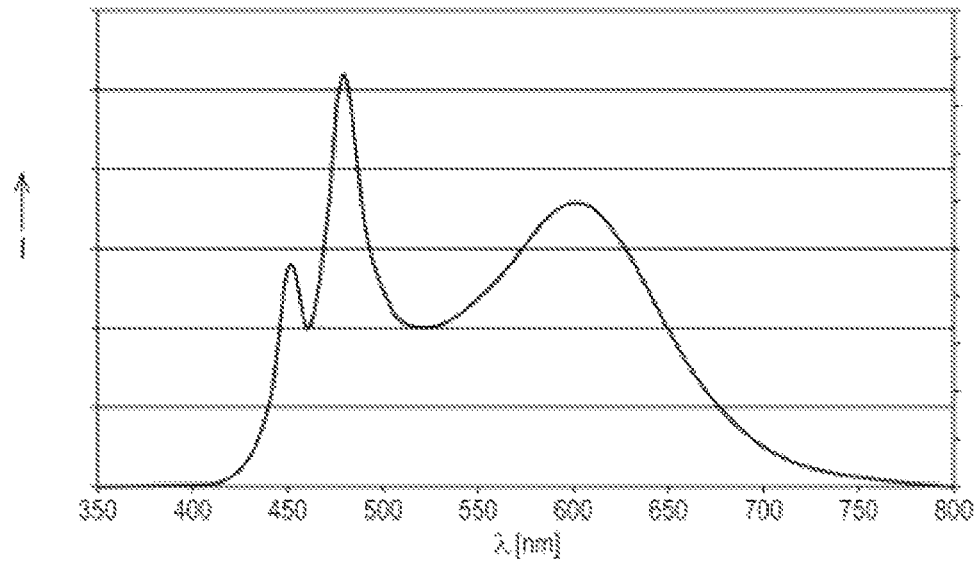
FIG. 1 shows a spectrum of a high MDER solution, showing a second peak in the Cyan range around 480 nm.

Solutions to increase the melanopic lux (or Melanopic Daylight Efficiency Ration—MDER) may e.g. require a peak in the cyan light around 480 nm (FIG. 1). Creating such spectrum requires a different LED solution than standard white LEDs.

In the present invention, amongst others for HCL luminaires it is desired replacing the white (solid state) light source with a light source optimized for melanopic boost. In the present invention, this implies in embodiments that cyan LEDs are added. Amongst others, in embodiments the micro lens optics+diffuser based architecture may result in an acceptable uniform color, but the solution with a lens may results in visibility of the cyan LEDs. This may be undesired, as the preference of end users may be to have a smooth color uniform exit window. In general, it appears to be preferred not have visible cyan dots or artefacts.

Figure 2:
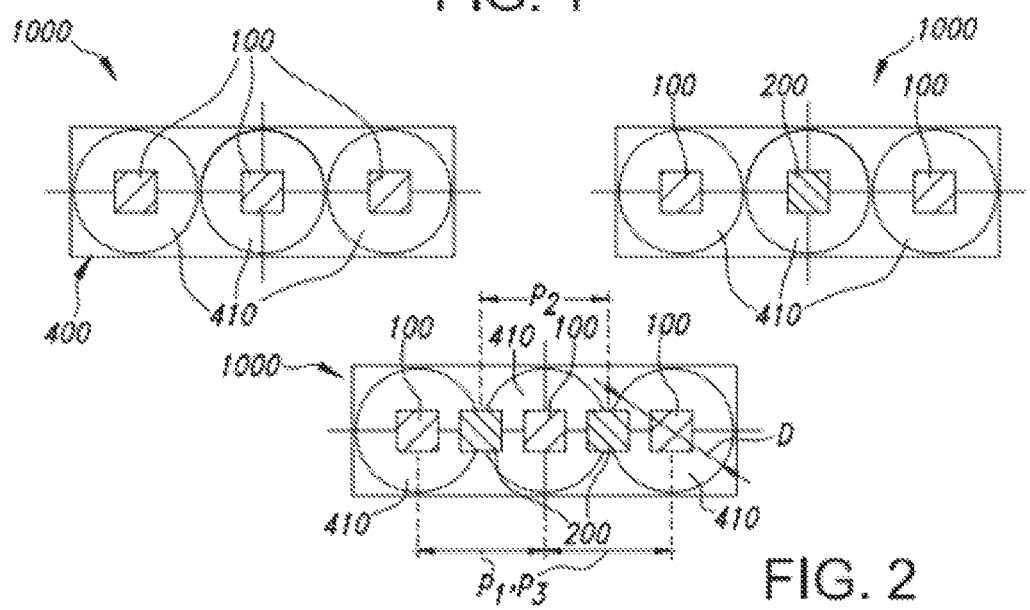
FIG. 2: Left side: standard white 3D lens based optical architecture, middle: when adding a cyan LED, right side: when increasing the LED count, but the lenses cannot be smaller and put closer to each other.

As indicated above, there may be some disadvantages in applying a 3D lens based solution: by adding cyan light, or making a tunable white/cyan LEDs on a support, more LEDs may be needed on the support. But the dimension of an efficient 3D lens may be linked to the size of the LED package. Typically a 3D lens requires a diameter of 10 mm, or larger, for 3 mm wide packages. That means that placing the packages close together (as in cyan added support), there may essentially be no space for efficient 3D lenses. This problem is indicated in FIG. 2. The right hand side shows that adding more LEDs results in a conflict with the minimum size of the lenses.

As described before, there may be a conflict between low glare and high vertical illuminance. The melanopic boost light may especially be measured in vertical illuminance, but adding the cyan LEDs underneath lenses may be done for glare reduction and actually reduces the vertical illuminance of the emitted cyan light.

The invention may include a support with both white and cyan LEDs, and lens plates with lenses only on the white LEDs and (essentially) not on the cyan LEDs. As a result, the white light may essentially be collimated and optimized for glare and horizontal illumination, whilst the cyan light (typically only 10% of the total) may essentially not be collimated and may have higher vertical illuminance.

Several cases were studied. A first study case of adding cyan is "case A", where both white and cyan have the same optical shape to be collimated (the center drawing of FIG. 2), all of horizontal illuminance, vertical illuminance and UGR will be the same as original single white LED, see left drawing in FIG. 2) because in this case, there is no change on photometry distribution. However, because of the spectral change by adding the cyan LED, the melanopic efficiency ratio is increased, as well as the melanopic vertical illuminance. In this case, with a certain amount of added cyan, the melanopic ratio of both vertical illuminance and horizontal illuminance to a viewer e.g. increase from MDER=0.6 (white light) to MDER=0.87 (white+cyan light). This may just be the consequence of the new spectrum with more cyan.

In FIG. 2, reference 1000 refers to a light generating system; reference 100 refers to a first light source, especially a solid state light source. Reference 200 refers to a second light source, especially a solid state light source. reference 400 refers to optics and reference 410 refers to beam shaping elements. In FIG. 2 (on the left), first light sources 100 are depicted, with optics 400 comprising beam shaping elements 410, for each light source 100. In FIG. 2, on the right a series of two first light sources 100 with in between a second light source 200 is depicted, with the optics 400 comprising beam shaping elements 410, for each of the first light sources 100 and the second light source 200. The lower drawing in FIG. 2 schematically depicts the same embodiment as in the upper left embodiment, but with second light sources 200 configured between the first light sources 100. Hence, the pitches of the first light sources and second light sources are essentially the same. Therefore, in the lower drawing of FIG. 2, an embodiment of the light generating system 1000 is schematically depicted, wherein the second light sources 200 in a second array and the beam shaping elements 410 are configured such that for a plurality of the second light sources 200 in the second array may apply that part of its second light source light propagates through a first beam shaping element 410 configured downstream of a first adjacent first light source 100 and part of its second light source light propagates through a second beam shaping element 410 configured downstream of a second adjacent first light source 100. Hence, in this schematically depicted embodiment, the first light sources 100 may be configured in a first array having a second pitch P1 and the second light sources 200 may be configured in a second array having a second pitch P2. The optics 400 may in embodiments comprise a plurality of beam shaping elements 410 configured to beam shape at least the first light source light. Especially, the beam shaping elements 410 may be configured in a third array having a third pitch P3. The beam shaping elements 410 may have a first diameter D. Especially, P1=P3. Further, especially P2≥P1. Yet further, especially $0.6 \leq D/P1 \leq 1$.

Figure 3:
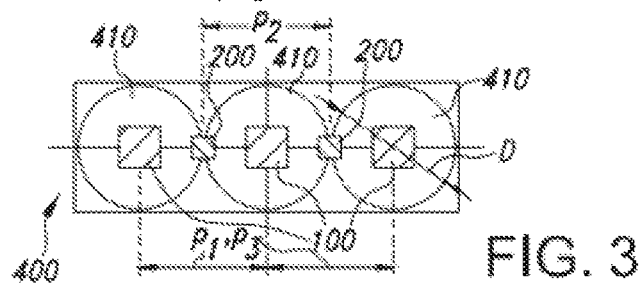
FIG. 3: Example of the invention where (smaller) cyan LEDs (or less intense LEDs) are placed in between the collimating lenses for the white LEDs.

In the present invention, especially the cyan light does not have the same optical shape as the white light. As indicated in FIG. 3, the cyan LEDs are placed in between the white LEDs but without their own lens. In this case, the photometry distribution of cyan will be changed.

For reference purposes, an optical design is chosen which is not necessarily optimized. The intensity in different view angles were evaluated.

In embodiments, though not mandatory, one may use many cyan LEDs. In case the distance between the cyan LEDs is large (large pitch) there may be a visible pixilation of the cyan LEDs. By using small(er) cyan LEDs, with lower light output, more cyan LEDs may be needed. This may be advantageous for placing them in between the lenses. In the melanopic boost spectrum, the cyan light is around 10% of the total lumen. Instead of or in addition to smaller cyan LEDs, also cyan LEDs may be used which are configured at a larger pitch. Further, smaller may especially indicate less power.

Herein, in embodiments the resulting radiation pattern from the lenses may show (equal to or) less than 10% cyan light in the horizontal direction, and more than 10% in the vertical direction.

Figure 4:
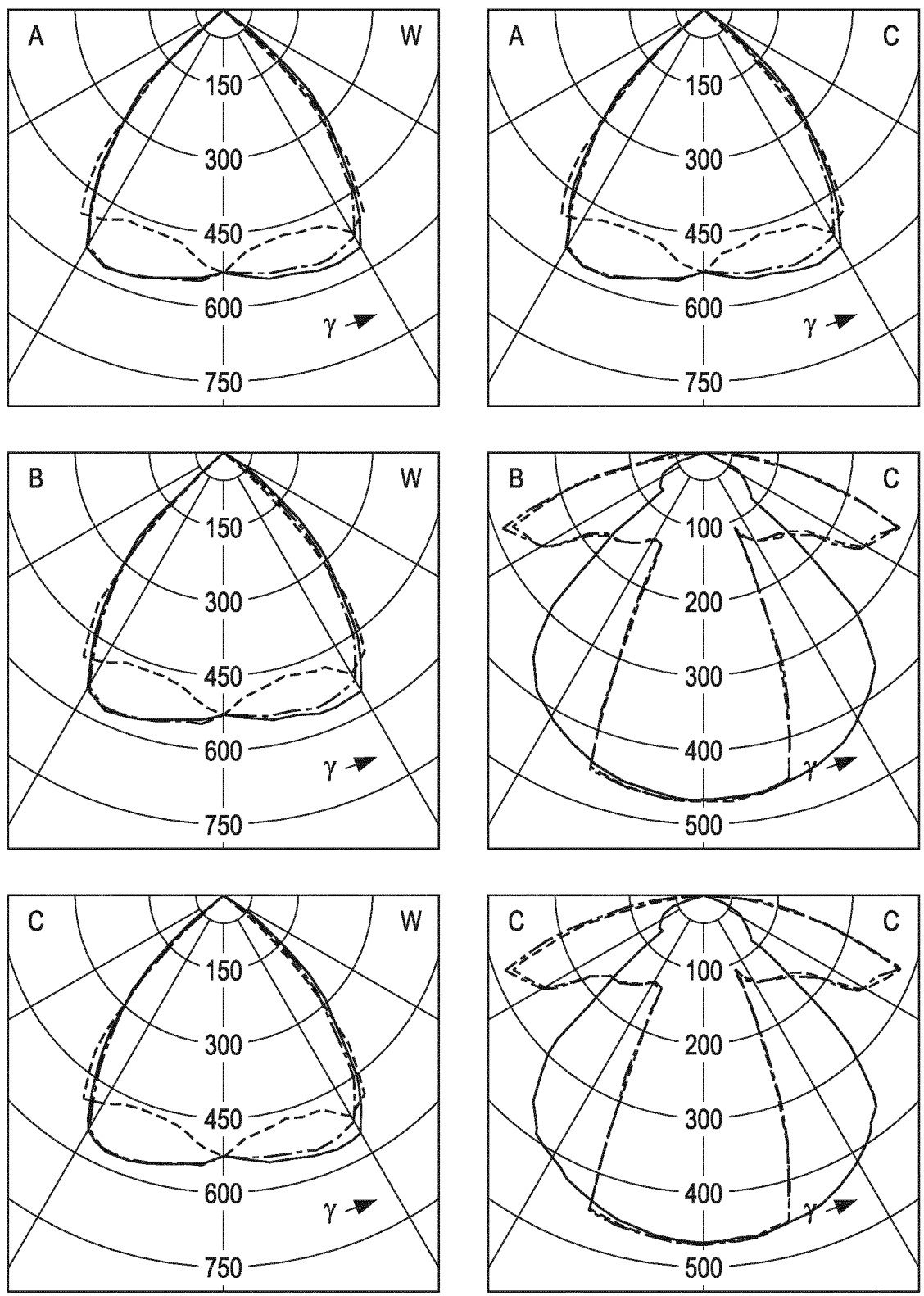
FIG. 4: depicts some polar plots.

The inventors modelled the light distribution with different solutions of the cyan emitter placed between the lenses. In "case B", see FIG. 2, lower embodiment or FIG. 3, the total UGR increases as a result of both cyan and white light being influenced by the opening on top of the cyan LED in between the white LEDs. This opening creates a reflection interfaces, and light rays are reflected (TIR reflection). The total UGR (sum of white and cyan light) may increase from 18 to 20 (in this non-optimized embodiment). FIG. 4 shows the result of the light intensity at different viewing angles. For reference, the first row indicates the original white LEDs with original lens plate (case A). A low intensity is found at highest angles. When adding cyan LEDs between the lenses, we find more light at larger angles (see cases B and C). As indicated above, modelling was done using an example lens. Different lens designs may result in different UGR values. Here, non-optimized results are shown. In FIG. 4, the full curves indicate the 0-180° plane, the dashed curves indicate the 90-270° plane, and the dot-dashed curves indicate a plane in between. W in the upper right corner refers to the polar plots for the white light (embodiment of first light source light) and C the upper right corner refers to the cyan light (embodiment of second light source light). Case C may be closer to application than case B, as in this non-optimized example the cyan content may be relatively large. Referring also to FIG. 4, the following data were retrieved:

| View angle (°) | 0 | 55 | 60 | 65 | 70 | 80 |
| --- | --- | --- | --- | --- | --- | --- |
| Mono white (left of FIG. x1) | 526 cd/klm | 53 cd/klm | 20 cd/klm | 14 cd/klm | 18.5 cd/klm | 7.5 cd/klm |
| Case A cyan in lens (middle of FIG. x1) | 526 cd/klm | 53 cd/klm | 20 cd/klm | 14 cd/klm | 18.5 cd/klm | 7.5 cd/klm |
| Case B cyan in between (FIG. x2) | 524 cd/klm | 70.4 cd/klm | 30 cd/klm | 42 cd/klm | 60 cd/klm | 94 cd/klm |

-continued

| View angle (°) | 0 | 55 | 60 | 65 | 70 | 80 |
|---|---|---|---|---|---|---|
| Case C cyan in between (FIG. x2 (and see further below)) | 520 cd/klm | 67.6 cd/klm | 38.5 cd/klm | 39.6 cd/klm | 41.2 cd/klm | 27 cd/klm |

In order to understand the contribution from white and cyan, we need to split the ratio of intensity. And in table 1, case A, case B and Case C indicates the intensity distribution from different viewing angles, which will all contribute to illuminance in certain position. There is no significant difference of intensity at 0° but a large difference at 80° viewing angle. FIG. 4 shows the intensity contribution from white and cyan, using the polar plots. A clear difference between the original lens (Case A) and without lens is visible in the polar intensity of the cyan. To indicate the difference of the cyan ratio in Eh and Ev, one view angle was taken to explain the impact. Here, the view angle 80° was taken (and compared with 0°).

The angles 0° and 80° may for instance be chosen because it may show essentially the biggest difference on intensity.

Figure 5:
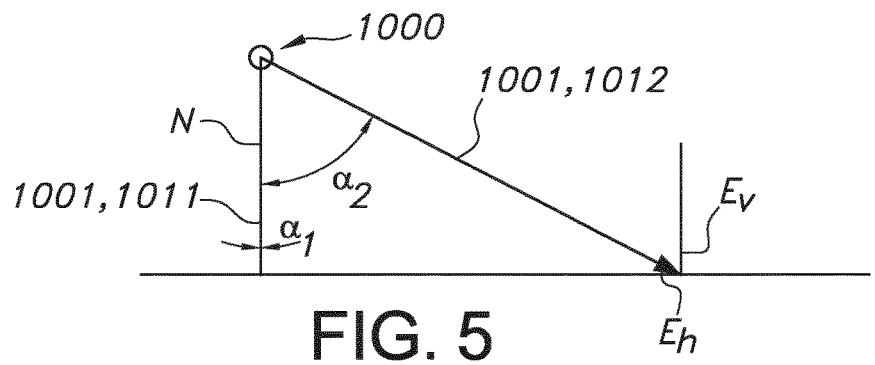
FIG. 5 schematically depict different viewing angles.

According to the function between intensity and illuminance, the horizontal and vertical illuminance in certain view angles can be calculated when considering the contribution from a single luminaire, see also FIG. 5. Herein, a mounting height of 3 m to work out the illuminance from white and cyan is assumed. Angle α1 refers to system light 1001 having angle α1 to the normal N. Especially, angle α1 is 0°. Referring to e.g. FIG. 2 (lower embodiment, FIG. 3, FIGS. 8b, 8e and 8f, the normal N may especially be perpendicular to the plane of drawings (see e.g. also FIGS. 8a and 8c)). This system light 1001 is especially indicated as first system light 1011. Angle α2 refers to system light 1001 having angle α2 to the normal N. α2≠α1. The spectral power distribution of the system light 1001 under angle α2 may especially be different from the spectral power distribution of the first system light 1011. This system light 1001 is especially indicated as second system light 1012. In embodiments, |α1−α2|=80°±5°.

Values were determined for a view angle of 0° and a view angle of 80°. Further, amongst others the MDER was evaluated (see below tables). As indicated above, the system may further be optimized.

Both tables show that in case B and C the cyan component is strongly reduced at 0 degree, and increased at 80° viewing angle. As a consequence, the MDER value at large angle is strongly increased.

In FIG. 5, N refers to a normal to the light generating system 1000. Reference 1001 refers to the system light. In different directions, the system light 1001 may have different spectral power distributions. Reference α1 refers to a first angle with the normal N, under which first system light 1011 propagates; reference α2 refers to a second angle with the normal N, under which second system light 1012 propagates.

Especially, the light generating system 1000 may be configured to provide in a first operational mode white first system light 1011 in a first direction and second system light 1012 in a second direction. In embodiments, the first system light 1011 in the first direction comprises the first light source light and the second light source light 201. Further, in embodiments the first system light 1011 has a first ratio R1 of luminous flux in the second wavelength range relative to the luminous flux in the first wavelength range; and the second system light 1012 in the second direction at least comprises the second light source light, wherein the second system light 1012 has a second ratio R2 of luminous flux in the second wavelength range relative to the luminous flux in the first wavelength range. Especially, R2/R1>1. In embodiments, under a first angle α1 relative to a normal N to the light generating system 1000 the first ratio R1 is selected from the range of 0.01-0.15. Further, in embodiments under a second angle α2 relative to the normal N to the light generating system 1000 the second ratio R2 is selected from the range of 0.2-15. Especially, in embodiments |α1−α2|=80°±5°. Further, in specific embodiments wherein R2/R1 may be selected from the range of 0.2-5.

The large Eh/klm_cyan and Ev/klm_cyan values at 80° for case B and C in the above example relates to one luminaire and with this specific lens example. We can further

| View angle 0° | Eh/klm | Eh/klm_white | Eh/klm_cyan | Eh ratio Cyan/White | Ev/klm | Ev/klm_white | Ev/klm_cyan | Ev ratio Cyan/white |
|---|---|---|---|---|---|---|---|---|
| Mono white | 58.4 | 58.4 | 0 | | 0 | 0 | 0 | NA |
| Case A | 58.4 | 52.56 | 5.84 | 1:9 | 0 | 0 | 0 | NA |
| Case B | 58.2 | 57.6 | 0.6 | 1:93 | 0 | 0 | 0 | NA |
| Case C | 57.8 | 57.2 | 0.6 | 1:103 | 0 | 0 | 0 | NA |

| View angle 80° | Eh/klm | Eh/klm_white | Eh/klm_cyan | Eh ratio Cyan/White | Ev/klm | Ev/klm_white | Ev/klm_cyan | Ev ratio Cyan/white | MDER |
|---|---|---|---|---|---|---|---|---|---|
| Mono white | 0.14 | 0.14 | 0 | 0 | 0.796 | 0.796 | 0 | | 0.61 |
| Case A | 0.14 | 0.122 | 0.014 | 1:9 | 0.796 | 0.7164 | 0.0796 | 1:9 | 0.87 |
| Case B | 1.75 | 0.125 | 1.625 | 13:1 | 9.97 | 0.713 | 9.257 | 13:1 | 4.87 |
| Case C | 0.5 | 0.12 | 0.38 | 3:1 | 2.86 | 0.66 | 2.2 | 3:1 | 3.28 | finetune the ratio of cyan:white at larger angles, for example by a lower overall cyan intensity. Which can be realized with smaller cyan LEDs or less cyan LEDs. Also we can optimize the lens designs further to adjust the polar plots indicated in FIG. 4.

In addition, in reality e.g. an (office) room may be equipped with many luminaires. As a consequence the real Ev value in an office may have a lower cyan ratio at different locations in the room than indicated in the table for case B and C, but still a much higher than the value in case A. The real value may depend on the specific room, luminaire type and luminaire configurations.

Figure 6:
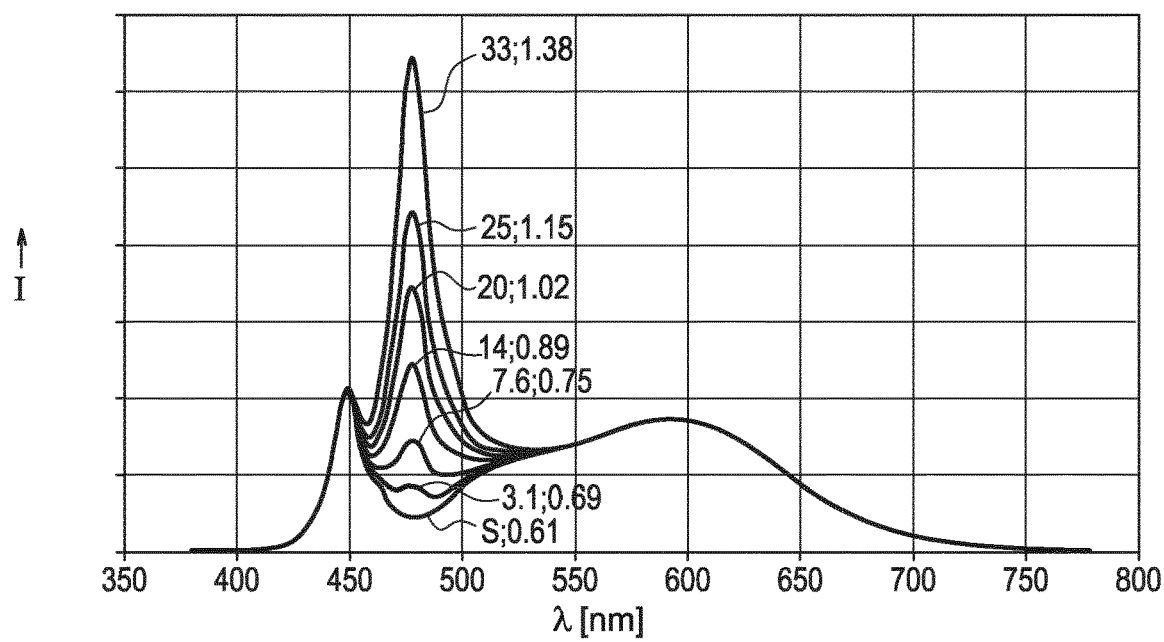
FIG. 6: Shows a spectra and MDER values for various intensities of cyan light added in the white spectrum of a 4000 K white LED.

In FIG. 6, the impact of a larger cyan contribution to the MDER value is indicated. As an example, a standard 4000 K white LED spectrum is taken, having an MDER of 0.61. Upon adding larger fractions of cyan, the MDER value increases. The cyan itself would have an MDER value of about 5.7. It is expected that increasing the cyan ratio from 1:9 to 1:4 realizes an MDER increase from about 0.87 to about 1.15. As can be seen in FIG. 6, the second light source light, defined by the cyan peak, may have a dominant wavelength within the 470-490 nm wavelength range. Also the peak wavelength is within this wavelength range.

Referring to FIG. 6, the x-axis indicates the wavelength (nm) and the y axis the intensity, in arbitrary units. The references to the curves first indicate the percentage % of the second light relative to the first light, on the basis of lumens. The second value after the semi colons indicates the respective MDER value. Reference S indicates a reference spectrum of white light having a CRI of 80 and a CCT of 4000 K, which has an MDER value of 0.61. This reference spectrum is essentially white light. As indicated above, white light may especially be used as first light source light. In embodiments, such as in this example, the second light source light may essentially be cyan light.

Case B and case C in the above table may not meet a more desirable ratio for MDER requirement. For instance, would one desire an MDER of 1.15, one may need to fine tune the flux ratio of cyan/white, not 1:9 any longer. See for instance case C and referring to the observation angle of 80°, and we keep the same light distribution.

For instance, the ratio of cyan/white may be changed into 1:124, see e.g. the table below. Then, an MDER value of 1.15 may be achieved. Hence, a smaller cyan flux may provide the desired MDER at e.g. 80°.

| View angle 80° | Eh/klm | Eh/klm_white | Eh/klm_cyan | Eh ratio Cyan/White | Ev/klm | Ev/klm_white | Ev/klm_cyan | Ev ratio Cyan/white | MDER |
|---|---|---|---|---|---|---|---|---|---|
| Case C | 0.5 | 0.4 | 0.1 | 1:4 | 2.86 | 2.28 | 0.58 | 1:4 | 1.15 |

From the above, it can be concluded that the cyan/white ratio (ratio of the power in the cyan wavelength range of 470-490 nm) relative to the total intensity of the system light, at angles of about 80°, may be selected from the range of about 1:5-5:1, such as 1:5-3:1.

Controlling the relative intensities may be done by controlling the number of second light sources relative to first light sources and/or by controlling the intensity of the second light sources relative to the first light sources. The former can be done when producing the system. The latter may be done during production of the system but may also be executed during operation of the system, such as by choosing the duty cycle and/or the power provided to the first light sources and/or second light sources.

In case C, a large improvement is made if the lens opening above the cyan LED is modified such that the light reflecting on the interface of that opening is Lambertian emitted from the interface surface. This may be realized by modifying the inner surface of the lens opening for the cyan LED, such as by adding textures. For example, this may be obtained by using a roughness treatment. Charmille VDI14 is good for it. In that case, the UGR with the cyan LED is 19 versus the original (non-cyan based) support of 18.

In all of the above documented solutions, the cyan LED may be replaced by an LED with a different wavelength/spectrum not being white. For example, LEDs with a peak emission in the range 390-425 nm are known to have a disinfection effect on bacteria, fungi, molds and spores. Adding LEDs within this range will add a disinfection or sanitizing function to the luminaire, where surfaces underneath the luminaire will be disinfected. Adding these deep blue wavelength LEDs in between the white LEDs can be advantageous, similar to the cases described above for adding cyan LEDs. These low wavelength LEDs have a very low contribution to the overall white light (e.g. 1% or less), and therefore the radiation pattern does not necessarily need to obey the rules for low UGR. As a result, there is no specific need for these deep blue LEDs to have the same light distribution as for the white LEDs. Therefore, these LEDs do not need to have a lens.

The fact that the radiation distribution for the non-white LEDs has more radiation to the large angles can be useful also for disinfection light. But for the cyan light it has the additional advantage that the Ev_MDER is increased, reaching a higher effectiveness for persons in the room. This advantage may be less necessarily needed for a disinfection spectrum.

Figure 7:
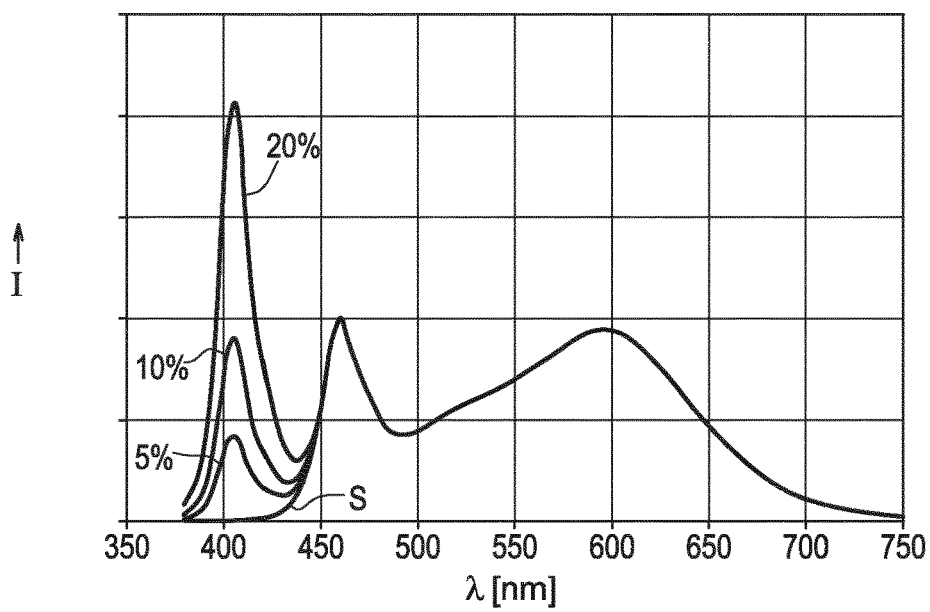
FIG. 7: Example of a spectrum of white light plus a 405 nm peak. The four spectra show an intensity contribution in the violet of 5%, 10% and 20% as well as without 405 nm. The white spectrum is CRI80/4000K (840)

An example of a white light spectrum with added 405 nm light is shown in FIG. 7. The added deep blue light is typically within the 10-30% of the total white light, but is not limited to this range. In a specific high intensity disinfection mode, the white light might be switched off and only deep blue light is on. A light source with this solution could be achieved by having alternating white and deep blue LEDs. According to this invention, the lens plate can have lenses on top of the white LEDs, and no specific lens on top of the deep blue LED. This can be a similar lens plate as described in the cases for the cyan light. In FIG. 7, the same reference S is applied. The percentages indicate the deep blue light peaking at about 405 nm relative to the white light, both on the basis of lumen.

Figure 8A:
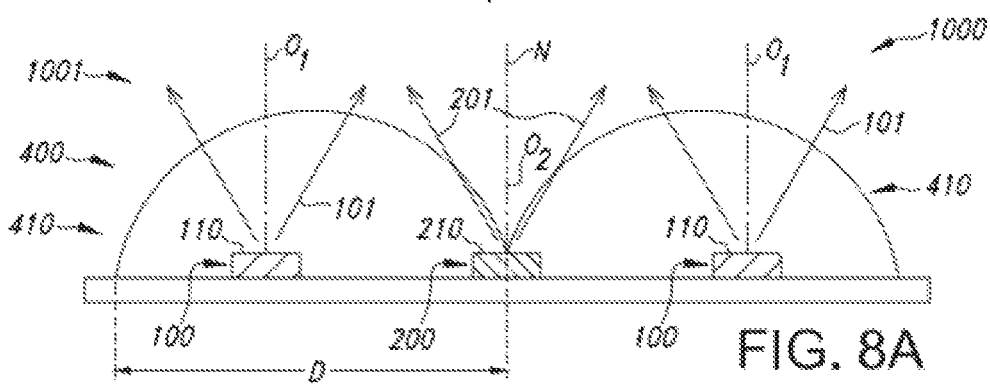
FIGS. 8*a*-8*f* schematically depict several embodiments and variants.

FIG. 8*a* schematically depicts an embodiment of the light generating system 1000 comprising a first light source 100, a second light source 200, and optics 400.

The first light source 100 is configured to generate first light source light 101 having in a first operational mode a first spectral power distribution. Especially, the first light source light 101 has at least intensity at a plurality of wavelengths in a first wavelength range of 380-780 nm. For instance, the first light source light may be white light.

The second light source 200 is configured to generate second light source light 201 having in the first operational mode a second spectral power distribution differing from the first spectral power distribution. In embodiments, the second light source light 201 has at least intensity at one or more wavelengths in a second wavelength range of one or more of (i) 380-430 nm and (ii) 470-490 nm, such as in the range of 470-490 nm (especially cyan light). Hence, in embodiments the second light source light 201 has at least intensity at one or more wavelengths in the second wavelength range of 470-490 nm.

In embodiments, the first light source light 101 is white light, and at least 80% of the total power (in the visible wavelength range) of the second light source light 101 is within the second wavelength range, and wherein the second light source light 201 has a dominant wavelength selected from the range of 478-484 nm.

The optics 400 are especially configured to beam shape at least the first light source light 101. In embodiments, the optics 400 may comprise a plurality of beam shaping elements 410. Especially, the beam shaping elements 410 are configured downstream of the first light sources 100. In embodiments, the beam shaping elements 410 are selected from the group consisting of lenses, reflectors and collimators. As schematically depicted, the beam shaping elements 410 may in embodiments also at least partly be configured downstream of the second light sources 200.

Especially, the light generating system 1000 is configured to generate system light 1001. In one or more operational modes, the system light 1001 may be white light, optionally enriched with light at one or more wavelengths in a second wavelength range of one or more of (i) 380-430 nm and (ii) 470-490 nm, such as in the range of 470-490 nm (especially cyan light).

Further, referring to FIG. 8a, the first light source 100 may have a first light emitting face 110 and a first optical axis O1 configured perpendicular to the light emitting face 110. Yet further, the second light source 200 has a second light emitting face 210 and a second optical axis O2 configured perpendicular to the second light emitting face 210. Especially, in embodiments the first optical axis O1 and the second optical axis O2 may be configured colinear. Reference D indicates the (equivalent circular) diameter.

Further, especially the first light source 100 is a solid state light source and the second light source 200 is a solid state light source.

Hence, amongst others FIG. 8a schematically depicts an embodiment wherein the first light sources 100 have first light emitting faces 110, such as LED dies, and first optical axes O1 configured perpendicular to the light emitting faces 110. Further, amongst others FIG. 8a schematically depicts an embodiment wherein the second light sources 200, here only one schematically depicted, have second light emitting faces 210 and second optical axes O2 configured perpendicular to the second light emitting faces 210, such as LED dies, wherein the first optical axes O1 and the second optical axes O2 are configured colinear. Especially, the first light sources 100 are solid state light sources and the second light sources 200 are solid state light sources.

Figure 8B:
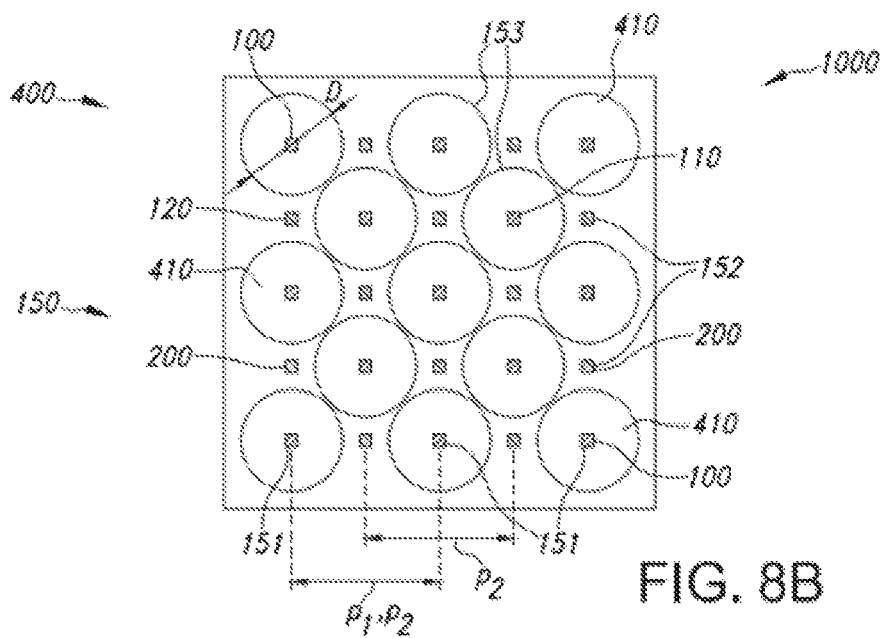

Referring to FIG. 8b, the light generating system 1000 may comprise a plurality of first light sources 100 and a plurality of second light sources 200. Further, the first light sources 100 and the second light sources 200 may be configured in an array 150. Especially, in embodiments one or more first light sources 100 alternate with one or more second light sources 200. In embodiments the plurality of first light sources 100 are configured in a first array 151 and the plurality of second light sources 200 are configured in a second array 152. In embodiments, the first light sources 100 in the first array 151 have a first pitch P1. In embodiments, the second light sources 200 in the second array 152 have a second pitch P2. In embodiments, the optics 400 may comprise a plurality of beam shaping elements 410 configured in a third array 153. In embodiments, the beam shaping elements 410 in the third array 153 have a third pitch P3. In specific embodiments, P1=P3. In embodiments, the beam shaping elements 410 have a first (equivalent circular) diameter D. In embodiments, $0.6 \leq D/P1 \leq 1$. Further, in embodiments $0.9 \leq D/P1 \leq 1$. Especially, $P2 \leq 3.5$ cm. The second light sources 200 in the second array 152 and the beam shaping elements 410 (in the third array 153) may be configured such that for a plurality of the second light sources 200 in the second array 152 applies that part of its second light source light 201 propagates through a first beam shaping element 410 configured downstream of a first adjacent first light source 100 and part of its second light source light 201 propagates through a second beam shaping element 410 configured downstream of a second adjacent first light source 100. Further, for the second light sources 200 within the plurality of second light sources 200 may apply that they are configured between the (respective) first adjacent first light source 100 and the (respective) second adjacent first light source 100. FIG. 8b schematically depicts 2D arrays.

Figure 8C:
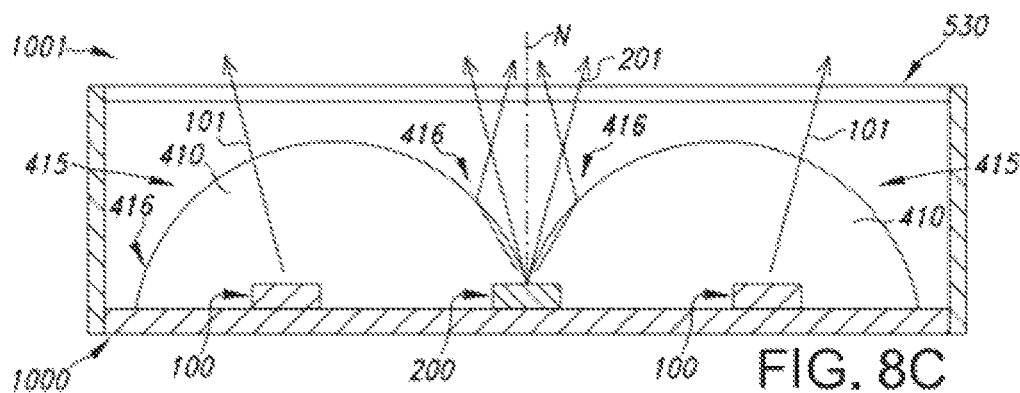

Referring to FIG. 8c, in embodiments the light generating system 1000 may further comprise a diffusor 530 configured downstream of the beam shaping elements 410. Essentially all light (of the first light source 100 and of the second light source) reaching the diffusor may be transmitted through the diffusor, such as over 95%. The diffusor may include scattering structures, such as e.g. in the case of a translucent window. For instance, the diffusor 530 may be of polycarbonate. The diffusor may comprise an optical plate or an optical foil. In embodiments the beam shaping elements 410 comprise lenses 415. Further, the lenses 415 may comprise lens edges 416. Especially, the second light sources 200 and the lenses 415 may be configured such that part of the second light source light 201 propagates through the lens edges 416. In specific embodiments, the lens edges 416 may have a higher roughness than the lenses 416 have in average.

Figure 8D:
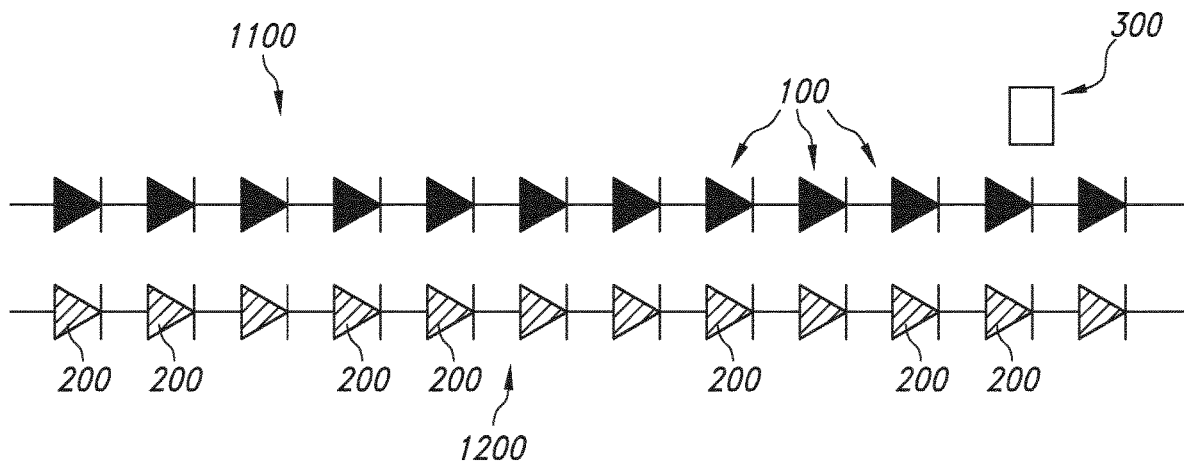

Referring to FIG. 8d, the light generating system 1000 may comprise a first LED string 1100 comprising the plurality of first light sources 100 and a second LED string 1200 comprising the plurality of second light sources 200. Yet further, the light generating system 1000 may comprise a control system 300 configured to control the first LED string 1100 and the second LED string 1200 (individually).

Figure 8E:
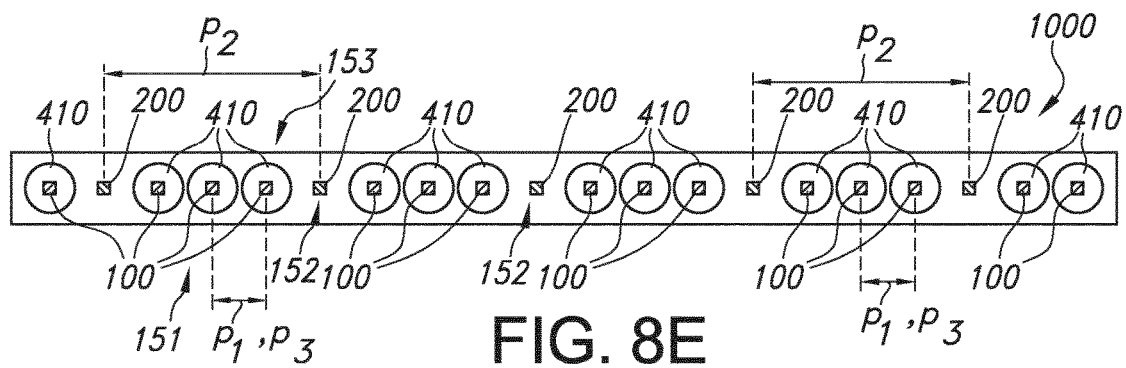

FIG. 8e schematically depicts an embodiment with a linear array of first light sources 100 (and second light sources 200) and beam shaping elements 410. Here, P1=P3. By way of example P2>P1. However, especially P2 may be equal to or less than about 3.5 cm. In the embodiment of FIG. 8e, there are no beam shaping elements 410 downstream of the second light sources 200.

Figure 8F:
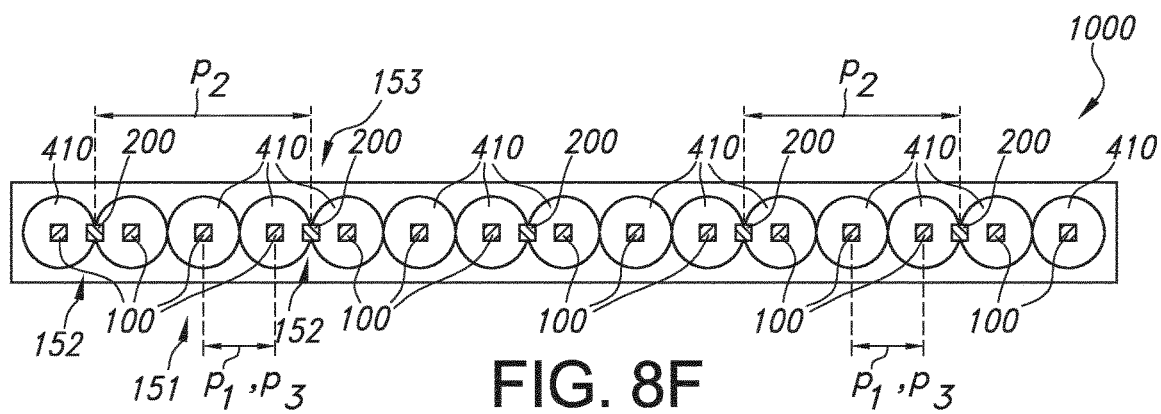

FIG. 8f is a variant on the embodiments of FIG. 2, lowest embodiment and FIG. 3. Here, the second light sources 200 in a second array and the beam shaping elements 410 are configured such that for a plurality of the second light sources 200 in the second array may apply that part of its second light source light propagates through a first beam shaping element 410 configured downstream of a first adjacent first light source 100 and part of its second light source light propagates through a second beam shaping element 410 configured downstream of a second adjacent first light source 100. Hence, in this schematically depicted embodiment, the first light sources 100 may be configured in a first array having a second pitch P1 and the second light sources 200 may be configured in a second array having a second pitch P2. The optics 400 may in embodiments comprise a plurality of beam shaping elements 410 configured to beam shape at least the first light source light. Especially, the beam shaping elements 410 may be configured in a third array having a third pitch P3. The beam shaping elements 410 may have a first diameter D. Especially, P1=P3. Further, especially P2≥P1. Yet further, especially 0.6≤D/P1≤1.

Referring to FIGS. 8e-8f, downstream of the second light source there may be no lens or downstream of the second light source there may be part of one or more adjacent lenses that are configured to collimate the first light source light of adjacent first light sources.

Figure 9:
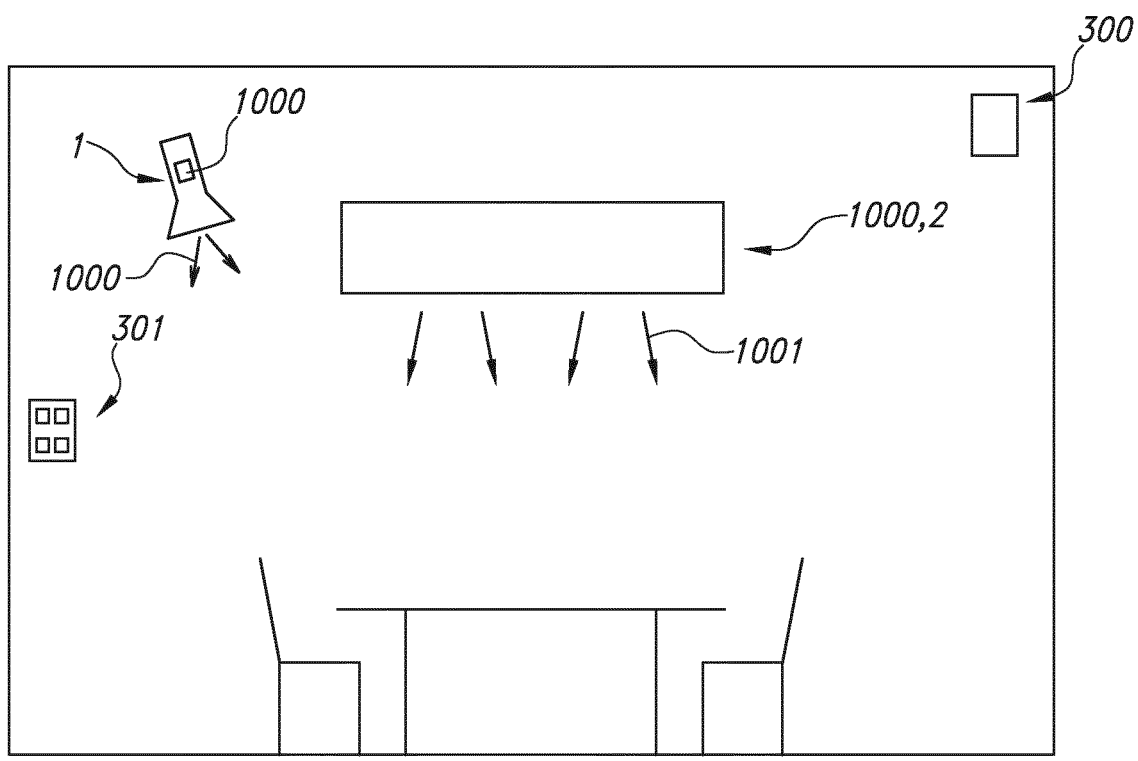
FIG. 9 schematically depicts a luminaire and a lamp. The schematic drawings are not necessarily to scale.

FIG. 9 schematically depicts an embodiment of a luminaire 2 comprising the light generating device 1000 as described above. Reference 301 indicates a user interface, such as a graphical user interface, which may be functionally coupled with the control system 300 comprised by or functionally coupled to the lighting system 1000. FIG. 9 also schematically depicts an embodiment of lamp 1 comprising the light generating device 1000.

Amongst others, the invention may be applied for office lighting, school lighting, hospital lighting, airplane lighting, consumer lamps that promote healthy lighting and concentration lighting (for studying, home-office, etc.), lighting having a disinfection function, etc.

The term "plurality" refers to two or more.

The terms "substantially" or "essentially" herein, and similar terms, will be understood by the person skilled in the art. The terms "substantially" or "essentially" may also include embodiments with "entirely", "completely", "all", etc. Hence, in embodiments the adjective substantially or essentially may also be removed. Where applicable, the term "substantially" or the term "essentially" may also relate to 90% or higher, such as 95% or higher, especially 99% or higher, even more especially 99.5% or higher, including 100%.

The term "comprise" also includes embodiments wherein the term "comprises" means "consists of".

The term "and/or" especially relates to one or more of the items mentioned before and after "and/or". For instance, a phrase "item 1 and/or item 2" and similar phrases may relate to one or more of item 1 and item 2. The term "comprising" may in an embodiment refer to "consisting of" but may in another embodiment also refer to "containing at least the defined species and optionally one or more other species".

Furthermore, the terms first, second, third and the like in the description and in the claims, are used for distinguishing between similar elements and not necessarily for describing a sequential or chronological order. It is to be understood that the terms so used are interchangeable under appropriate circumstances and that the embodiments of the invention described herein are capable of operation in other sequences than described or illustrated herein.

The devices, apparatus, or systems may herein amongst others be described during operation. As will be clear to the person skilled in the art, the invention is not limited to methods of operation, or devices, apparatus, or systems in operation.

It should be noted that the above-mentioned embodiments illustrate rather than limit the invention, and that those skilled in the art will be able to design many alternative embodiments without departing from the scope of the appended claims.

In the claims, any reference signs placed between parentheses shall not be construed as limiting the claim.

Use of the verb "to comprise" and its conjugations does not exclude the presence of elements or steps other than those stated in a claim. Unless the context clearly requires otherwise, throughout the description and the claims, the words "comprise", "comprising", and the like are to be construed in an inclusive sense as opposed to an exclusive or exhaustive sense; that is to say, in the sense of "including, but not limited to".

The article "a" or "an" preceding an element does not exclude the presence of a plurality of such elements.

The invention may be implemented by means of hardware comprising several distinct elements, and by means of a suitably programmed computer. In a device claim, or an apparatus claim, or a system claim, enumerating several means, several of these means may be embodied by one and the same item of hardware. The mere fact that certain measures are recited in mutually different dependent claims does not indicate that a combination of these measures cannot be used to advantage.

The invention also provides a control system that may control the device, apparatus, or system, or that may execute the herein described method or process. Yet further, the invention also provides a computer program product, when running on a computer which is functionally coupled to or comprised by the device, apparatus, or system, controls one or more controllable elements of such device, apparatus, or system.

The invention further applies to a device, apparatus, or system comprising one or more of the characterizing features described in the description and/or shown in the attached drawings. The invention further pertains to a method or process comprising one or more of the characterizing features described in the description and/or shown in the attached drawings.

The various aspects discussed in this patent can be combined in order to provide additional advantages. Further, the person skilled in the art will understand that embodiments can be combined, and that also more than two embodiments can be combined. Furthermore, some of the features can form the basis for one or more divisional applications.

The invention claimed is:

1. A light generating system comprising:
   a plurality of first light sources configured to generate first light source light having a first spectral power distribution in a first operational mode, the first light source light having at least a plurality of wavelengths in a first wavelength range of 380-780 nm, and are configured in a first array having a first pitch (P1);
   a plurality of second light sources are configured to generate second light source light having a second spectral power distribution in the first operational mode, the second spectral power distribution differing from the first spectral power distribution, the second light source light having at least intensity at one or more wavelengths in a second wavelength range of 470-490 nm, and are configured in a second array having a second pitch (P2); and
   a plurality of beam shaping elements configured to beam shape at least the first light source light, the beam shaping elements configured in a third array having a third pitch (P3), and the beam shaping elements having a first diameter (D);

wherein:

P1=P3 and P2≥P1, the light generating system is configured to provide in the first operational mode white first system light in a first direction and second system light in a second direction, the first system light has a first ratio R1 of luminous flux in the second wavelength range relative to the luminous flux in the first wavelength range, the second system light has a second ratio R2 of luminous flux in the second wavelength range relative to the luminous flux in the first wavelength range, and under a first angle ($\alpha1$) relative to the light generating system the first ratio R1 is selected from the range of 0.01-0.15, under a second angle ($\alpha2$) relative to the light generating system the second ratio R2 is selected from the range of 0.2-15, the second angle is larger than the first angle, and the ratio R2/R1>1.

2. The light generating system according to claim 1, wherein 0.5≤D/P1≤1.

3. The light generating system according to claim 1, wherein R2 is selected from the range of 0.2-5.

4. The light generating system according to claim 1, wherein the first light source light is white light, and wherein at least 80% of the total power of the second light source light is within the second wavelength range, and wherein the second light source light has a dominant wavelength selected from the range of 478-484 nm.

5. The light generating system according to claim 1, wherein $|\alpha1-\alpha2|=80°\pm5°$.

6. The light generating system according claim 5, wherein the ratio R2/R1>2.

7. The light generating system according to claim 1, wherein the first light sources have first light emitting faces and first optical axes configured perpendicular to the light emitting faces, wherein the second light sources have second light emitting faces and second optical axes configured perpendicular to the second light emitting faces, wherein the first optical axes and the second optical axes are configured colinear; and wherein the first light sources are solid state light sources and wherein the second light sources are solid state light sources.

8. The light generating system according to claim 1, wherein the second light sources in the second array and the beam shaping elements are configured such that for a plurality of the second light sources in the second array applies that part of its second light source light propagates through a first beam shaping element configured downstream of a first adjacent first light source and part of its second light source light propagates through a second beam shaping element configured downstream of a second adjacent first light source.

9. The light generating system according to claim 1, comprising:

a first LED string comprising the plurality of first light sources;

a second LED string comprising the plurality of second light sources;

a control system configured to control the first LED string and the second LED string.

10. A luminaire comprising a housing, and the light generating system according to claim 1.

11. The light generating system according to claim 1, wherein the beam shaping elements comprise lenses, wherein the light generating system further comprises a diffusor configured downstream of the beam shaping elements.

12. The light generating system according to claim 11, wherein the lenses comprise lens edges, wherein the second light sources and the lenses are configured such that part of the second light source light propagates through the lens edges, wherein the lens edges have a higher roughness than the lenses have in average.

13. The light generating system according to claim 1, wherein one or more first light sources alternate with one or more second light sources, and wherein the beam shaping elements are configured downstream of the first light sources.

14. The light generating system according to claim 13, wherein the beam shaping elements are selected from the group consisting of lenses, reflectors and collimators.

15. The light generating system according to claim 13, wherein the beam shaping elements are also at least partly configured downstream of the second light sources.

* * * * *